United States Patent [19]

Lee et al.

[11] Patent Number: 5,677,457
[45] Date of Patent: Oct. 14, 1997

[54] METHOD OF PREPARATION OF PHYSOSTIGMINE CARBAMATE DERIVATIVES FROM ESEROLINE ETHERS

[75] Inventors: Thomas B. K. Lee, Whitehouse Station; Zhongli Gao, Somerville; Barbara S. Rauckman, Flemington, all of N.J.

[73] Assignee: Hoechst Marion Roussel, Inc., Cincinnati, Ohio

[21] Appl. No.: 769,409

[22] Filed: Dec. 19, 1996

[51] Int. Cl.[6] ................................. C07D 487/00
[52] U.S. Cl. ..................... 546/141; 546/147; 548/429
[58] Field of Search ......................... 546/141, 147; 548/429

[56] References Cited

U.S. PATENT DOCUMENTS

| | | | |
|---|---|---|---|
| 4,791,107 | 12/1988 | Hamer et al. | 514/228.2 |
| 4,831,155 | 5/1989 | Brufani et al. | 548/429 |
| 4,914,102 | 4/1990 | Glamkowski | 514/232.8 |
| 4,937,341 | 6/1990 | Glamkowski | 544/142 |
| 4,971,992 | 11/1990 | Glamkowski et al. | 514/411 |
| 4,983,616 | 1/1991 | O'Malley et al. | 514/339 |
| 5,077,289 | 12/1991 | Glamkowski et al. | 514/211 |
| 5,081,117 | 1/1992 | Glamkowski et al. | 514/216 |
| 5,091,541 | 2/1992 | O'Malley et al. | 548/429 |
| 5,153,193 | 10/1992 | Flanagan et al. | 514/228.8 |
| 5,173,497 | 12/1992 | Flanagan | 514/411 |
| 5,177,101 | 1/1993 | Glamkowski et al. | 514/411 |
| 5,187,165 | 2/1993 | Hamer et al. | 514/307 |
| 5,216,017 | 6/1993 | Allen et al. | 514/411 |
| 5,231,093 | 7/1993 | Flanagan et al. | 514/215 |
| 5,234,941 | 8/1993 | Flanagan et al. | 514/411 |
| 5,260,452 | 11/1993 | Glamkowski et al. | 548/486 |
| 5,264,587 | 11/1993 | Flanagan | 548/429 |
| 5,274,117 | 12/1993 | Lee et al. | 548/486 |
| 5,302,721 | 4/1994 | Wong et al. | 548/429 |
| 5,350,762 | 9/1994 | Martin et al. | 514/411 |
| 5,387,695 | 2/1995 | Lee et al. | 548/486 |
| 5,455,354 | 10/1995 | Wong et al. | 546/147 |
| 5,498,726 | 3/1996 | Lee et al. | 548/429 |
| 5,541,216 | 7/1996 | Hamer et al. | 514/411 |
| 5,541,340 | 7/1996 | Hamer et al. | 548/429 |
| 5,547,977 | 8/1996 | Hamer et al. | 514/41.1 |
| 5,550,254 | 8/1996 | Hamer et al. | 548/429 |
| 5,591,864 | 1/1997 | Glamkowski et al. | 548/429 |

FOREIGN PATENT DOCUMENTS

| | | |
|---|---|---|
| 0253372 | 1/1988 | European Pat. Off. . |
| 2905054 | 8/1980 | Germany . |
| 9200072 | 1/1992 | WIPO . |

OTHER PUBLICATIONS

Fieser & Fieser, Reagents for Organic Synthesis, pp. 451–452 (1976).
Organic Syntheses, Collective vol. 3, pp. 753–756 (1955).
Dakin, Am. Chem. J. 42, 447 pp. 150–153 (1909).

*Primary Examiner*—Joseph McKane
*Assistant Examiner*—Richard S. Myers, Jr.
*Attorney, Agent, or Firm*—William R. Boudreaux

[57] ABSTRACT

The present invention relates to a novel process for the preparation of physostigmine carbamate derivatives and to pharmaceutically acceptable salts thereof. The present invention further relates to a novel process for the preparation of eseroline derivatives and to pharmaceutically acceptable salts thereof.

21 Claims, 2 Drawing Sheets

Water (mL per g of eserethole)

Relative ratio of LiBr/HBr

METHOD OF PREPARATION OF PHYSOSTIGMINE CARBAMATE DERIVATIVES FROM ESEROLINE ETHERS

BACKGROUND OF THE INVENTION

The present invention relates to a novel process for the preparation of physostigmine carbamate derivatives and to pharmaceutically acceptable salts thereof. The present invention further relates to a novel process for the preparation of eseroline derivatives and to pharmaceutically acceptable salts thereof.

The physostigmine carbamate derivatives encompassed by the compounds of formula (I) below are useful as memory-enhancing and analgesic agents as disclosed in U.S. Pat. No. 4,791,107, issued Dec. 13, 1988; U.S. Pat. No. 5,187,165, issued Feb. 19, 1993; U.S. Pat. No. 5,541,216, issued Jul. 30, 1996; and U.S. Pat. No. 5,547,977, issued Aug. 20, 1996. The eseroline derivatives encompassed by the compounds of formula (III) are useful as memory-enhancing and analgesic agents as disclosed in U.S. Pat. No. 5,541,216, issued Jul. 30, 1996; Canadian Pat. No. 1,137,489, issued Dec. 14, 1982; and as useful intermediates for making additional memory-enhancing and analgesic agents.

Various methods for the preparation of physostigmine carbamate derivatives are known. See, for example, Hamer et al., U.S. Pat. No. 3,791,107; Brufani et al., U.S. Pat. No. 4,831,155; Wong et al., U.S. Pat. No. 5,302,721; and Wong et al., U.S. Pat. No. 5,455,354. There remains a need, however, for processes providing higher yields, ecologically allowed reagents and/or less costly means for obtaining these compounds.

An object of the present invention, therefore, is to provide novel methods for the economic preparation of physostigmine carbamate derivatives and to eseroline derivatives without the need for ecologically unfavorable halogenated organic solvents.

SUMMARY OF THE INVENTION

This application relates to a novel process for the preparation of a product of the formula

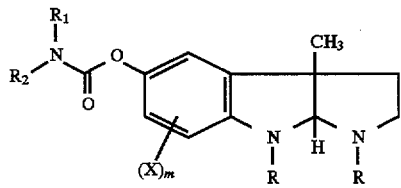

(I)

wherein

R is loweralkyl;

$R_1$ is hydrogen, loweralkyl, lowercycloalkyl, lowercycloalkylloweralkyl, lowerbicycloalkyl, aryl or arylloweralkyl;

$R_2$ is loweralkyl, lowercycloalkyl, lowercycloalkylloweralkyl, lowerbicycloalkyl, aryl or arylloweralkyl; or $R_1$ and $R_2$ taken together with the nitrogen atom to which they are attached form a group of the formula (Ia)

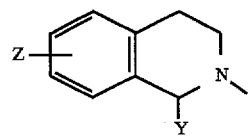

(Ia)

wherein

Y is hydrogen or loweralkyl and Z is hydrogen, loweralkyl, halogen, loweralkoxy or hydroxy;

X is loweralkyl, loweralkoxy, halogen or trifluoromethyl; and m is 0, 1 or 2;

or a pharmaceutically acceptable salt thereof; which process comprises (a) contacting a compound of formula (II)

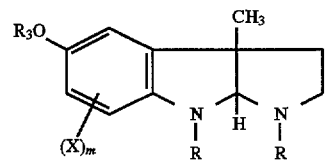

(II)

wherein

R, X and m are as defined above and $R_3$ is loweralkyl, with aqueous hydrogen bromide and lithium halide to afford a compound of formula (III)

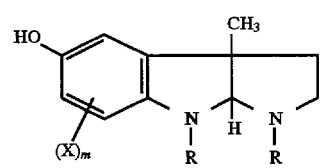

(III)

wherein

R, X and m are as defined above;

(b) contacting the reaction mixture containing the compound of Formula (III) either (1) with an isocyanate of the formula $R_1NCO$ and isolating a product of formula (I) wherein $R_2$ is hydrogen; or (2) with a compound of formula (IV)

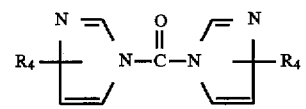

(IV)

wherein $R_4$ is hydrogen or loweralkyl to afford a compound of formula (V)

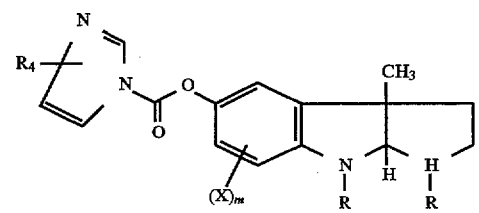

(V)

wherein

R, $R_4$, X and m are as above;

(c) contacting the reaction mixture containing the compound of formula (V) obtained in step (b) with a compound of the formula $R_1R_2NH$ wherein $R_1$ and $R_2$ are as above in the presence of a carboxylic acid of the formula $R_5COOH$ wherein $R_5$ is loweralkyl; and forming and isolating the product of formula (I).

This application further provides a novel process for the preparation of a product of formula (III)

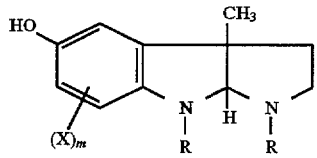

wherein

R is loweralkyl;

X is loweralkyl, loweralkoxy, halogen or trifluoromethyl; and m is 0, 1 or 2;

or a pharmaceutically acceptable salt thereof; comprising contacting a compound of formula (II)

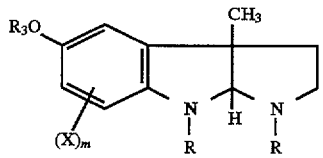

wherein

R, X and m are as defined above and $R_3$ is loweralkyl, with aqueous hydrogen bromide and lithium halide to afford a compound of formula (III).

DETAILED DESCRIPTION OF THE PREFERRED EMBODIMENTS

Figure 1:
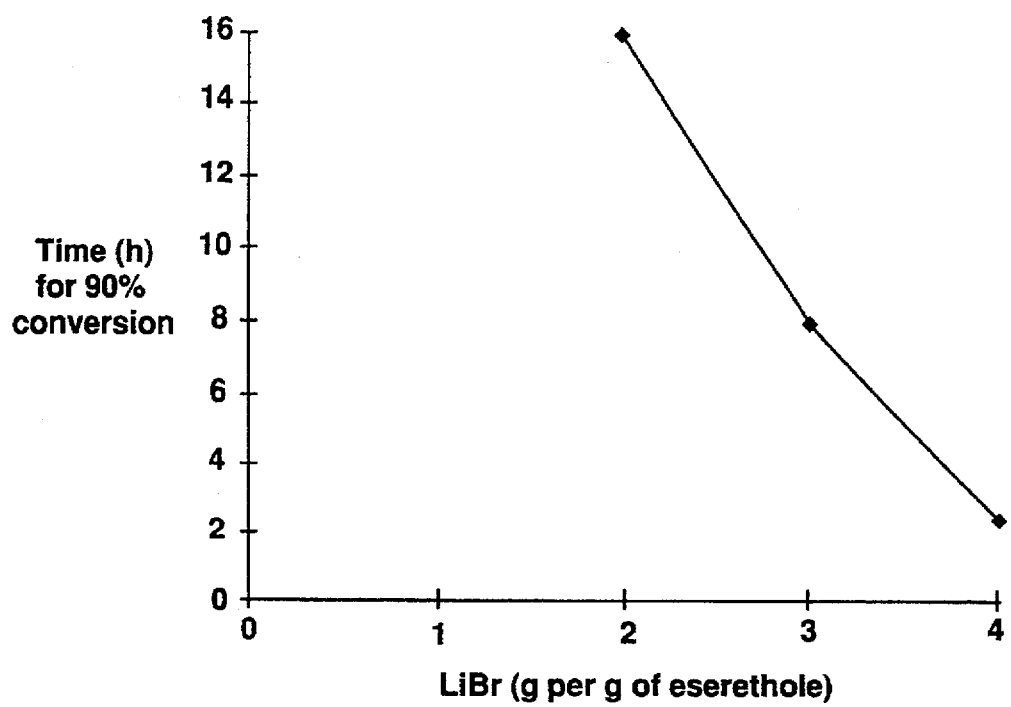
FIG. 1 shows the effect of lithium bromide (LiBr) in aqueous (aq.) hydrogen bromide (HBr) on the O-dealkylation of eserethole.

Unless otherwise stated or indicated, the term loweralkyl means a straight or branched alkyl group having from 1 to 6 carbon atoms. Examples of alkyl include methyl, ethyl, n-propyl, isobutyl, pentyl, hexyl, and the like.

Unless otherwise stated or indicated, the term lowercycloalkyl means a saturated ring containing 3 to 7 carbon atoms. Examples of lowercycloalkyl include cyclopropyl, cyclohexyl, cycloheptyl, and the like.

Unless otherwise stated or indicated, the term lowerbicycloalkyl means a group having two saturated rings which contain from 7 to 11 carbons and the rings are attached to each other through two carbons.

Unless otherwise stated or indicated, the term halogen means fluorine, chlorine, bromine or iodine.

Unless otherwise stated or indicated, the term halide means fluoride, chloride, bromide or iodide.

Unless otherwise stated or indicated, the term aryl means an unsubstituted phenyl or aromatic heterocyclic group; or a phenyl or aromatic heterocyclic group substituted with 1, 2 or 3 substituents each of which being independently loweralkyl, loweralkoxy, halogen, hydroxy, trifluoromethyl, phenoxy or benzyloxy.

The term "pharmaceutically acceptable salts" refers to acid addition salts. The expression "pharmaceutically acceptable acid addition salts" is intended to apply to any non-toxic organic or inorganic acid addition salt of the compounds of formula (I). Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hyroxymaleic, benzoic, hydroxybenzoic, phenylacetic, cinnamic, salicylic, 2-phenoxybenzoic, and sulfonic acids such as p-toluenesulfonic acid, methanesulfonic acid and 2-hydroxyethanesulfonic acid. Such salts can exist in either a hydrated or substantially anhydrous form.

Other methods for preparation of physostigmine carbamate derivatives are known. See, for example, Hamer et al., U.S. Pat. No. 3,791,107; Brufani et al., U.S. Pat. No. 4,831,155; Wong et al., U.S. Pat. No. 5,302,721; and Wong et al., U.S. Pat. No. 5,455,354. There remains a need, however, for processes providing higher yields, ecologically allowed reagents and/or less costly means for obtaining these compounds.

The process of this invention has the following major advantages over the previously known methods:

Aqueous hydrobromic acid is used as a dealkylating agent, along with lithium halide, as well as the reaction solvent. This reagent is less expensive than other previously used dealkylating agents such as boron tribromide or aluminum chloride.

No halogenated solvents are employed. Halogenated solvents such as dichloromethane or dichloroethane are environmentally undesirable and are not allowed by government regulations in many countries.

No preparative column chromatography purification is required. Preparative column chromatography is expensive, labor-intensive and limiting in scale-up throughput.

Environmental emission control is more effective as the lithium halide can be recycled.

Dilute acidic medium and mild reaction conditions decrease the risk of erosion.

The compounds of this invention are prepared by utilizing the synthetic steps described below. Throughout the description of the synthetic steps, the substituents "X", "Hal", "m", "R", "$R_1$", "$R_2$", "$R_3$", "$R_4$" and "$R_5$" shall have the respective meanings given above unless otherwise indicated.

In structural formulae depicting the compounds of this invention, heavy lines (⎯) coming out of the 3a-carbon and 8a-carbon of the 1,2,3,3a,8,8a-hexahydropyrrolo[2,3-b]

indole ring system signify that the two substituents are above the average plane of the three-ring system, whereas dotted lines (⋯) signify that the two substituents are below the average plane of the three-ring system, and wavy lines (∼) signify that the two substituents are both above said plane or below said plane. Because of conformational constraints, the two substituents at the 3a- and 8a-positions must be both above said average plane or both below said average plane. Thus, in formula (I), the substituents at the 3a- and 8a-positions are cis since they are on the same side of the three ring system. Where said substituents are both above the average plane of the three ring system, the configuration will be referred to as 3aS-cis and where both substituents are below the average plane of the ring, the configuration will be referred to as 3aR-cis. These two types of configurations are depicted below.

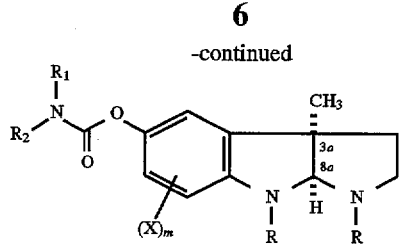

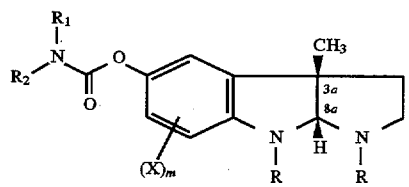

Both of said cis isomers, namely, the 3aS-cis isomer and the 3aR-cis isomer are encompassed by each given compound name or structural formula containing wavy lines mentioned above, Furthermore, all mixtures of the 3aS-cis and 3aR-cis isomers including the racemic mixture (1:1 ratio of 3aS-cis:3aR-cis) are encompassed.

SCHEME

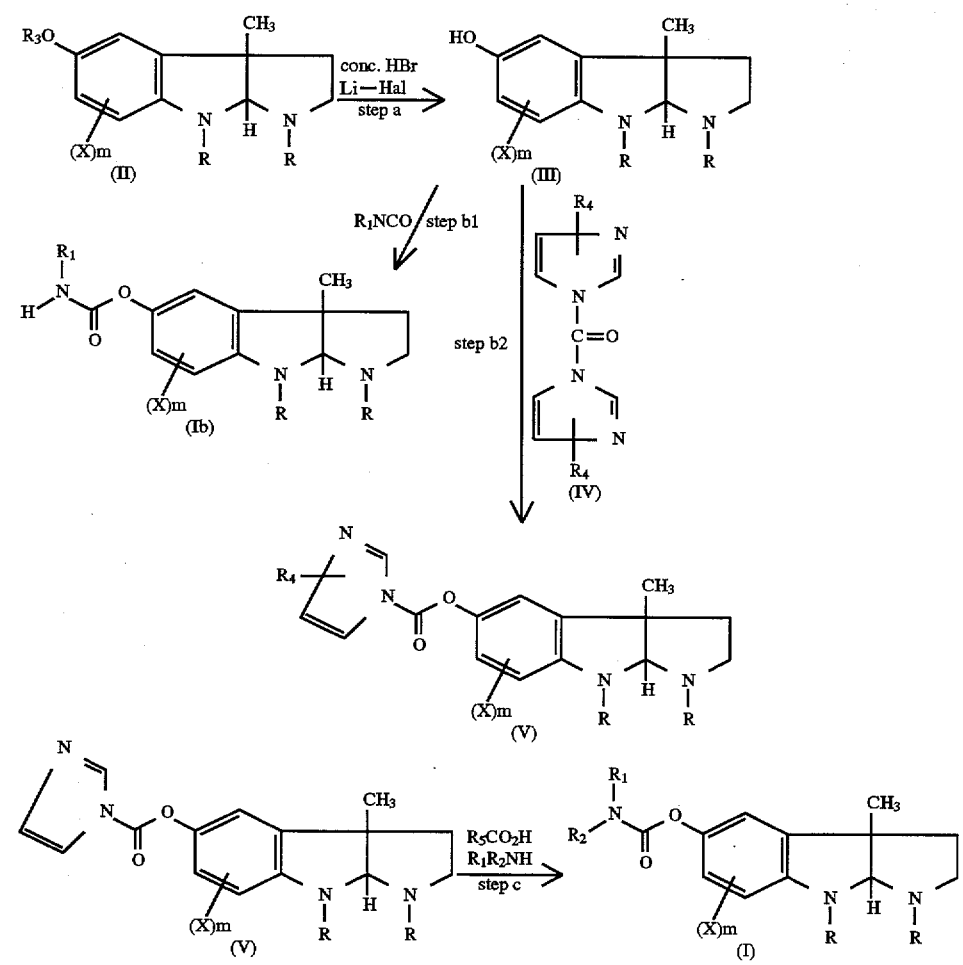

In step a, the compound of formula (II) is contacted with aqueous hydrogen bromide and lithium halide at room temperature. The reaction is then heated to a temperature ranging from 80° C.–100° C., preferably 90°–95° C., for a period of time ranging from 1 to 5 hours, preferably 3 to 4 hours. The reaction is then cooled, diluted with water and neutralized with a suitable base, for example, 10% lithium hydroxide or 20% potassium hydroxide. The appropriate compound of formula (III) is then extracted into an organic solvent such as butyl acetate or ethyl acetate and the resulting solution is dried with a drying agent such as potassium carbonate or molecular sieves.

In this application, the term "aqueous hydrogen bromide" is meant to encompass concentrations of hydrogen bromide of from about 20% to about 50%. Preferably, the hydrogen bromide concentration is 48% hydrogen bromide, which is commercially available. Lower concentrations of hydrogen bromide can be obtained from 48% hydrogen bromide by dilution with water. In this application, the term "lithium halide" is meant to encompass lithium bromide, lithium chloride and lithium iodide with lithium bromide being preferred.

In step b1, the compound of formula (III) is contacted with either an alkyl isocyanate or a substituted alkyl isocyanate to form a compound of Formula (I) where $R_2$ is hydrogen, as represented by structure (Ib) above. In this instance, the reaction temperature is generally between about 0° C. and about 25° C., preferably about 5° C. to about 10° C. The reaction is monitored and the pH is maintained between about 9 and 10 by the addition of a base such as, for example, potassium t-butoxide or an acid such as, for example, acetic acid.

In step b2, the compound of Formula (III) is contacted with the carbonyldiimidazole compound of Formula (IV) to provide the imidazole carbamate product of structure (V). In this instance, the addition is carried out at about 0° C. to about 25° C., preferably about 20° C.

In step c, the reaction is typically conducted by adding sequentially a carboxylic acid, such as, for example, acetic acid, and an amine such as tetrahydroisoquinoline to the solution obtained above. The pH of the acidic solution may optionally be acidified to a pH of from about 4.5 to about 6 with an acid, such as acetic acid, prior to contact with the appropriate amine. The addition of the amine is generally carried out from about −15° C. to about 25° C., preferably at from about −10° C. to about 20° C.

Examples of compounds made by the process of this invention include those listed below as well as the 3aR-cis isomers thereof and mixtures of the 3aS-cis and 3aR-cis isomers including the racemic mixtures:

(3aS-cis)-1,2,3,3a,8,8a-hexahydro-1,3a,8-trimethylpyrrolo[2,3-b]indol-5-ol, (1,2,3,4-tetrahydroisoquinolinyl) carbamate;

(3aS-cis)-1,2,3,3a,8,8a-hexahydro-1,3a,8-trimethylpyrrolo[2,3-b]indol-5-ol, (1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (1-ethyl-(1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (1-propyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (1-butyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-chloro-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (7-chloro-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-chloro-1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (7-chloro-1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-hydroxy-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (7-hydroxy-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-hydroxy-1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (7-hydroxy-1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, cyclohexyl carbamate ester;

(3aS-cis)-1,2,3,3a,8,8a-hexahydro-1,3a,8-trimethylpyrrolo[2,3-b]indol-5-ol, 3-chlorophenyl carbamate ester fumarate;

(3aS-cis)-1,2,3,3a,8,8a-hexahydro-1,3a,8-trimethylpyrrolo[2,3-b]indol-5-ol, 3-chlorophenyl carbamate ester; and (3aS-cis)-1,2,3,3a,8,8a-hexahydro-1,3a,8-trimethylpyrrolo[2,3-b]indol-5-ol, 1-(phenyl)ethyl carbamate ester.

The following examples are presented in order to illustrate the invention and are not to be construed as limiting the invention in any way.

EXAMPLE 1

Preparation of Eseroline Salicylic Salt

Dissolve LiBr (72 g) in water (36 mL) and 48% aq. HBr (40 mL). Cool the clear solution to an ice bath. To this cold solution add eserethole (20 g, 81.22 mmol). Warm the mixture and heat on an oil bath to 90°–100° C. for 3–5 h. Cool the mixture to room temperature and pour into ice water (600 mL). Neutralize the acidic solution with LiOH (10%) and extract with ethyl acetate (2×200 mL). Dry the combined extracts over potassium carbonate (40 g) and filter under nitrogen. The filtrate, containing eseroline (15.97 g, 90% by HPLC) can be used immediately for the preparation of (3aS-cis)-1,2,3,3a,8,8a-hexahydro-1,3a,8-trimethylpyrrolo[2,3-b]indol-5-ol, (1,2,3,4-tetrahydroisoquinolinyl)carbamate.

Mix the above solution (20 mL) with salicylic acid (0.55 g, 3.98 mmol, 1.1 eq.) in ethyl acetate (5 mL). Concentrate the clear solution to obtain gray crystals which are recrystallized from ethyl acetate to obtain pure eseroline salicylic salt.

Anal. Calcd. for $C_{20}H_{24}O_4N_2$: 67.40 C 6.79 H 7.86 N
Found: 67.50 C 6.77 H 7.86 N

EXAMPLE 2

Preparation of (3aS-cis)-1,2,3,3a,8,8a-hexahydro-1,3a,8-trimethylpyrrolo[2,3-b]indol-5-ol, (1,2,3,4-tetrahydroisoquinolinyl)carbamate a) Preparation of Eseroline Add LiBr (80 g) to 48% aq HBr (40 mL) and water (40 mL) to make a clear solution. To this solution add (−) eserethole (21.31 g, 86.63 mmol) at room temperature under nitrogen with stirring. Heat (90°–100° C.) the brownish clear solution with an oil bath for 5.5 hours. Cool the dark greenish brown solution to room temperature and pour into ice-water (240 mL). To this solution was add 20% LiOH to pH 9–10. Extract the mixture with ethyl acetate (2×150 mL). Wash the combined ethyl acetate solution with brine, dry over potassium carbonate and filter. Concentrate the filtrate (to 100 mL) to provide a residue which contains eseroline (17.76 g, 95% yield, 98.8% purity). This solution was used immediately in the preparation of the title product.

b) Preparation of (3aS-cis)-1,2,3,3a,8,8a-hexahydro-1,3a,8-trimethylpyrrolo[2,3-b]indol-5-ol, (1,2,3,4-tetrahydroisoquinolinyl/carbamate To the solution obtained in Example 2, step (a), add 1,1-carbonyldiimidazole (15.45 g, 95.29 mmol). Stir the reaction solution at room temperature for 15–30 min. To the same reaction mixture add acetic acid (15.59 g, 259.89 mmol, 3 equiv.) and 1,2,3,4-tetrahydroisoquinoline (12.69 g, 95.29 mmol, 1.1 equiv). Allow the mixture to stir overnight at ambient temperature under nitrogen. Wash the reddish reaction mixture with water (40 mL). The aqueous solution is then back extracted with ethyl acetate (40 mL). Extract the combined ethyl acetate extracts with dilute hydrochloric acid. Neutralize the combined acidic extracts with sodium hydroxide to pH 7.0 and extract with cyclohexane (2×120 mL). After drying with potassium carbonate, stir the solution with alumina (25 g), filter and concentrate to yield a residue crystallized from cyclohexane to obtain the title product (22.37 g, 68.42%) as a white granular crystalline solid (99.5% purity by HPLC); m.p.=77° C.

Anal. Calcd. for $C_{23}H_{27}O_2N_3$: 73.18 C 7.21 H 11.13 N
Found: 72.97 C 7.12 H 11.05 N

EXAMPLE 3

Preparation of (3aS-cis)-1,2,3,3a,8,8a-hexahydro-1, 3a,8-trimethylpyrrolo[2,3-b]indol-5-ol, (1,2,3,4-tetrahydroisoquinolinyl)carbamate Prepare by the method of Example 2 adding sequentially LiBr (36 g) and (−) eseretbole (10 g, 40.6 mmol) to a mixture of 18 mL water and 20 mL of aq HBr (48%). Heat the solution to 90°–100° C. and maintain for 5.5 hours.

EXAMPLE 4

Preparation of (3aS-cis)-1,2,3,3a,8,8a-hexahydro-1, 3a,8-trimethylpyrrolo[2,3-b]indol-5-ol, (1,2,3,4-tetrahydroisoquinolinyl)carbamate using lithium iodide To a mixture of LiI (3.08 g), water (2.0 mL) and 2.0 mL of aq HBr (48%) add eseretbole (0.5 g). Heat the mixture to 88°–95° C. for 7 hours. Pour the reaction mixture into ice water (10 mL) and basify with 50% potassium carbonate to pH 9–10. Extract the mixture with ethyl acetate (2×10 mL). Dry the combined extracts and filter. Prepare the title compound using the filtrate, containing eseroline (0.406 g, 91.8% purity) according to the method of Example 2.

EXAMPLE 5

Preparation of (3aS-cis)-1,2,3,3a,8,8a-hexahydro-1, 3a,8-trimethylpyrrolo[2,3-b]indol-5-ol, cyclohexyl carbamate ester To a solution of (−)-eseroline (2.2 g, from Example 2), there is added benzene (50 mL) containing cyclohexyl isocyanate (1.2 g) and the mixture is stirred at 25° C. for 3 hours. The product is isolated by extraction of the butyl acetate solution with water (200 mL) followed by sodium hydroxide solution (100 mL, 0.5N) and water (100 mL). The residue is dried over anhydrous sodium sulfate and the butyl acetate solution is concentrated under reduced pressure to yield the title compound.

EXAMPLE 6

Preparation of (3aS-cis)-1,2,3,3a,8,8a-hexahydro-1, 3a,8-trimethylpyrrolo[2,3-b]indol-5-ol, 3-chlorophenyl carbamate ester fumarate To a solution of (−)-eseroline (2.2 g, from Example 2), there is added 3-chlorophenyl isocyanate (1.5 g) over 1 hour at 5° C. and the mixture is stirred at 25° C. for 3 hours. The product is isolated as the fumarate salt following water washing, concentration under reduced pressure, chromatographic purification on silica gel and acidification of the purified free base with fumaric acid (1 equiv.).

EXAMPLE 7

Preparation of (3aS-cis)-1,2,3,3a,8,8a-hexahydro-1, 3a,8-trimethylpyrrolo[2,3-b]indol-5-ol, 3-chlorophenyl carbamate ester To a solution of (−)-eseroline (2.2 g, from Example 2), there is added 3-chlorophenyl isocyanate (1.6 g) at −5° C. over 5 minutes. After stirring for 0.25 hours, the title compound is isolated substantially as described in Example 2.

EXAMPLE 8

Preparation of (3aS-cis)-1,2,3,3a,8,8a-hexahydro-1, 3a,8-trimethylpyrrolo[2,3-b]indol-5-ol, 1-(phenyl) ethyl carbamate ester To a solution of (−)-eseroline (2.2 g, from Example 2), there is added (S)-(−)-α-methylbenzyl isocyanate (1.5 g) over 1.5 hours at 10° C. The title compound is isolated substantially as described in Example 2.

In many instances, O-dealkylation of eseroline ethers using 48% aqueous hydrogen bromide alone is not a suitable method. For example, the O-dealkylation requires too long a period of time for completion resulting in serious decomposition of the product. Table 1 discloses the O-dealkylation of eseretbole and esermethole using 48% aqueous hydrogen bromide.

TABLE 1

O-Dealkylation of Eseroline Ethers
Using 48% Aqueous Hydrogen Bromide Alone

| Compound | 48% HBr (mL/g) | Reaction Time (hours) | Remaining Starting Mat.* | Total Impurities (%) |
|---|---|---|---|---|
| Esermethole | 10 | 14.0 | 3.36 | 5.8 |
| Eseretbole | 10 | 14.0 | 9.40 | 35.96 |
| Eseretbole | 4 | 14.0 | 18.21 | 37.65 |

*Relative area by HPLC

The effects of varying reaction parameters of O-dealkylation of eseretbole were studied in such a way that in one set of experiments only one parameter varies while other parameters are kept unchanged. In all of these experiments, 1.00 g of eseretbole was heated at 95°–100° C. with variable amount of LiBr, water and aq. HBr while the overall volume of the reaction solution was maintained at 4.0 mL. The reaction was monitored by HPLC and the reaction time was represented as the time of 90% conversion of eseretbole in order to make an easier comparison. It was observed that the reaction rate of the O-dealkylation step increased as the amount of lithium bromide increased (FIG. 1). Table 2 illustrates the data obtained in this O-dealkylation reaction.

TABLE 2

| Entry | H$_2$O (mL) | LiBr Amount | Time (hours)* |
|---|---|---|---|
| 1 | 4 | 0 g | extremely long |
| 2 | 4 | 2.0 g (23.0 mmol, 5.7 eq.) | 11.0 |
| 3 | 4 | 3.0 g (34.5 mmol, 8.5 eq.) | 9.0 |
| 4 | 4 | 4.0 g (46.0 mmol, 11 eq.) | 2.3 |
| 5 | 0 | 0 | 20 |

*Time (h) for 90% completion with 1.00 g of eserethole, 4.0 mL of HBr (48%) at 95–100° C.

Figure 2:
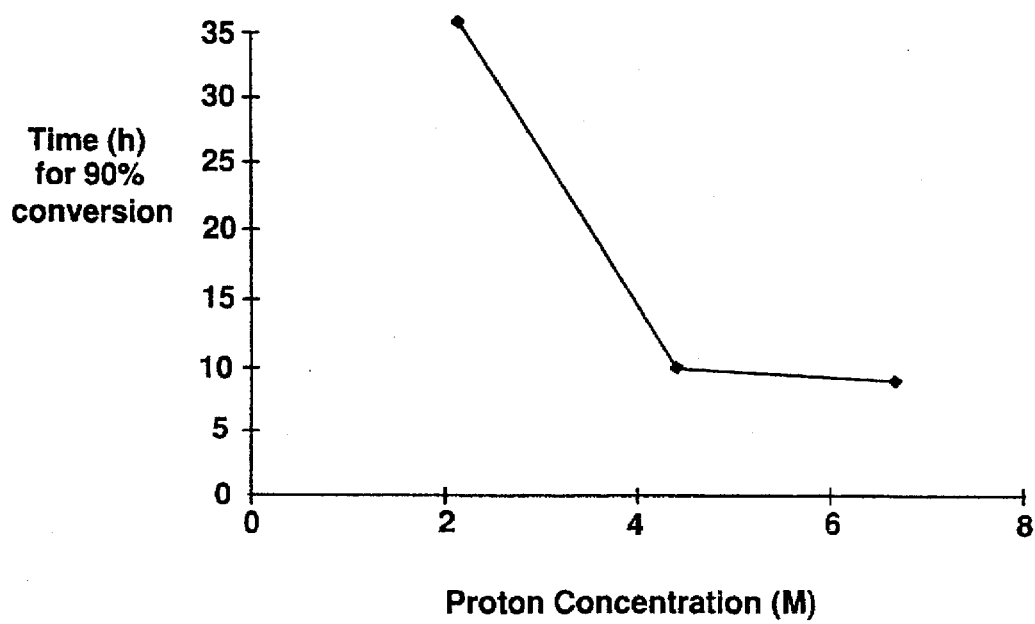
FIG. 2 shows the effect of acid strength on the O-dealkylation of eserethole.
Figure 3:
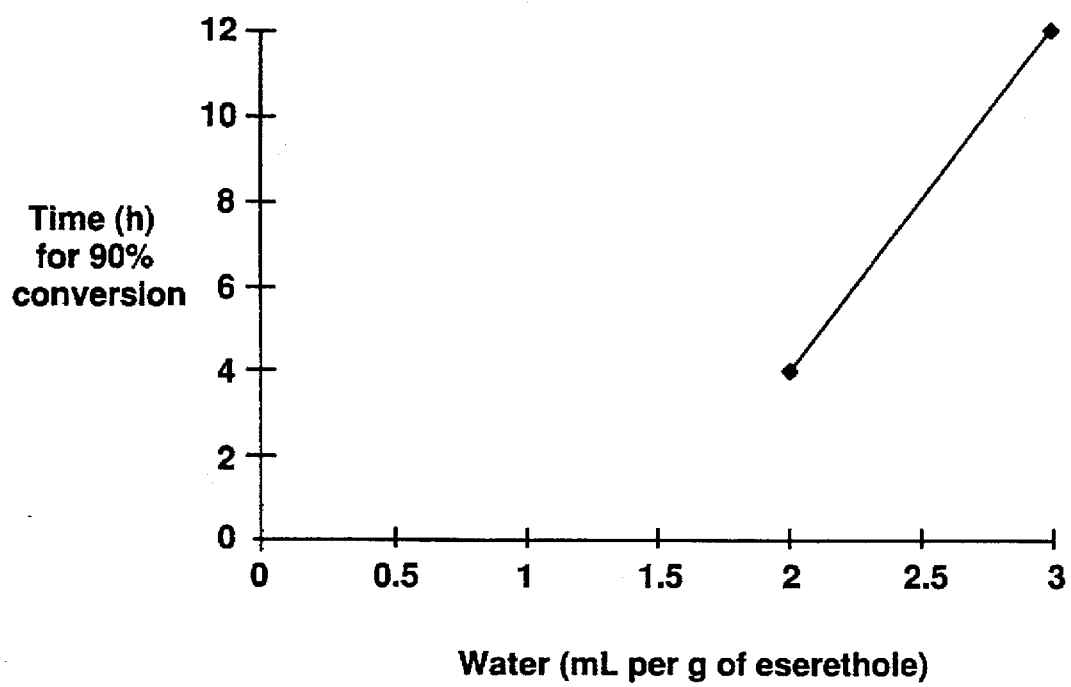
FIG. 3 shows the effect of water on the O-dealkylation of eserethole.
Figure 4:
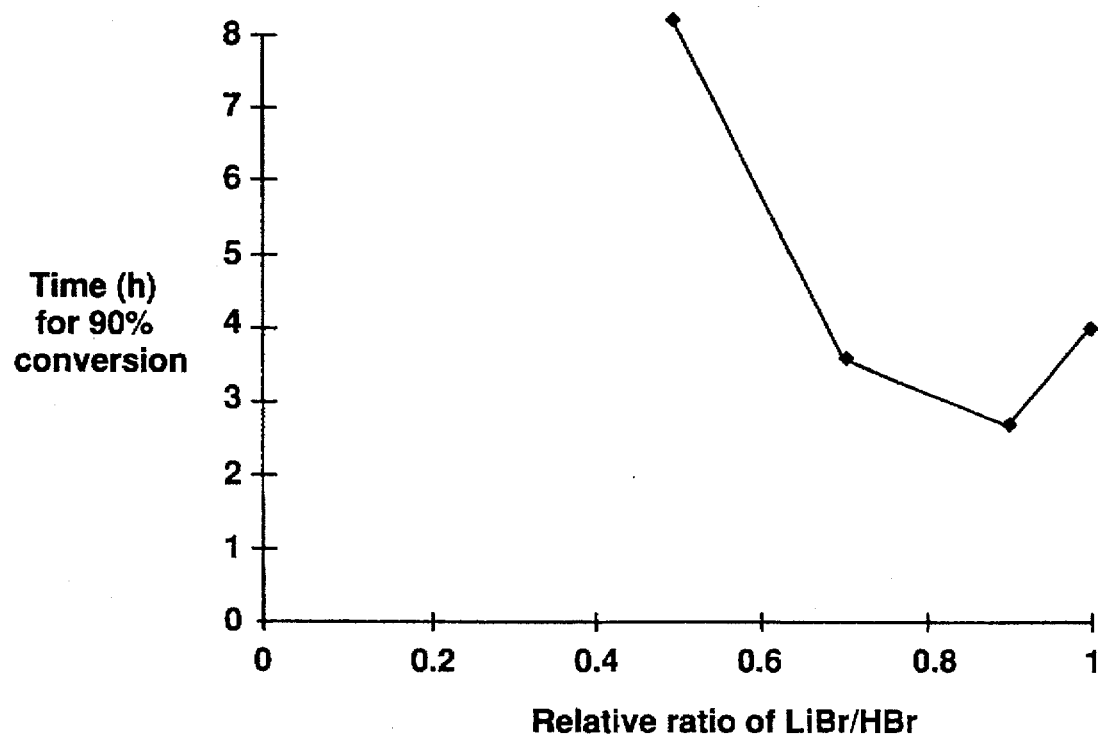
FIG. 4 shows the effect of the relative ratio of lithium bromide/hydrogen bromide on the O-dealkylation of eserethole.

Similarly, when acid strength was increased, the rate of reaction increased until a proton concentration of about 4.4M was reached. At that point, the reaction rate leveled off (FIG. 2). In contrast, dilution with water decreased the reaction rate (FIG. 3). The effect of the relative ratio of LiBr/HBr on the deprotection of eserethole is illustrated in FIG. 4.

The relative catalytic effects of various lithium halides as compared to other halides are as follows: LiBr>>NaBr>KBr; LiI>LiBr>>LiCl. Also, NH4Br, Eta$_3$NHBr, and LiCl showed no catalytic effect at all on O-dealkylation when the other conditions of the reaction were kept unchanged.

What is claimed is:

1. A process for the preparation of a compound of the formula

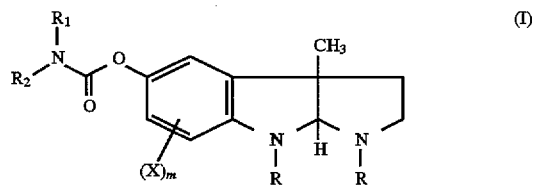

wherein

R is loweralkyl;

R$_1$ is hydrogen, loweralkyl, lowercycloalkyl, lowercycloalkylloweralkyl, lowerbicycloalkyl, aryl or arylloweralkyl;

R$_2$ is loweralkyl, lowercycloalkyl, lowercycloalkylloweralkyl, lowerbicycloalkyl, aryl or arylloweralkyl; or R$_1$ and R$_2$ taken together with the nitrogen atom to which they are attached form a group of the formula (Ia)

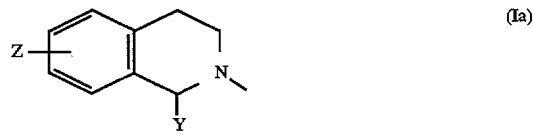

wherein

Y is hydrogen or loweralkyl and Z is hydrogen, loweralkyl, halogen, loweralkoxy or hydroxy;

X is loweralkyl, loweralkoxy, halogen or trifluoromethyl; and m is 0, 1 or 2;

or a pharmaceutically acceptable salt thereof;

which process comprises (a) contacting a compound of formula (II)

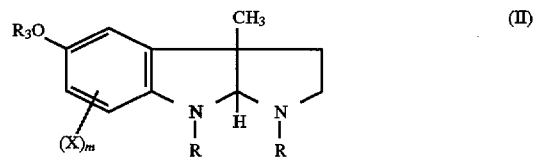

wherein

R, X and m are as defined above and R$_3$ is loweralkyl, with aqueous hydrogen bromide and lithium halide to afford a compound of formula (III)

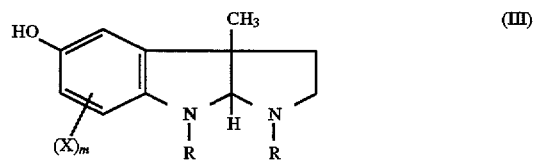

wherein

R, X and m are as defined above;

(b) contacting the reaction mixture having the compound of Formula (III) either (1) with an isocyanate of the formula R$_1$NCO and isolating a product of formula (I) wherein R$_2$ is hydrogen; or (2) with a compound of formula (IV)

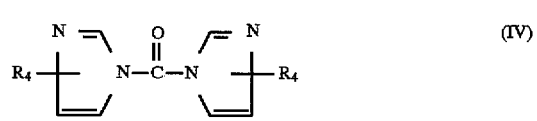

wherein

R$_4$ is hydrogen or loweralkyl to afford a compound of formula (V)

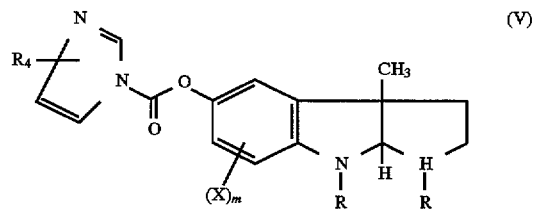

wherein

R, R$_4$, X and m are as above;

(c) contacting the reaction mixture having the compound of formula (V) obtained in step (b) with a compound of the formula

R$_1$R$_2$NH wherein

R$_1$ and R$_2$ are as above in the presence of a carboxylic acid of the formula

R$_5$COOH wherein

R$_5$ is loweralkyl; and forming and isolating the product of formula (I).

2. A process according to claim 1 wherein said lithium halide is lithium bromide.

3. A process according to claim 1 wherein said lithium halide is lithium iodide.

4. A process according to claim 1 wherein R and $R_3$ are loweralkyl and X is hydrogen.

5. A process according to claim 4 wherein R is methyl and $R_3$ is methyl.

6. A process according to claim 5 wherein the compound of formula (II) is (−)-eserethole.

7. A process according to claim 1 wherein R is loweralkyl, X is hydrogen and $R_1$ and $R_2$ together with the nitrogen to which they are attached form 1,2,3,4-tetrahydroisoquinoline group or a 1-methyl-1,2,3,4-tetrahydroisoquinoline group.

8. A process according to claim 7 wherein R is methyl.

9. A process according to claim 1 wherein said aqueous hydrogen bromide is hydrogen bromide with a concentration within the range of from about 20% to about 50%.

10. A process according to claim 1 wherein said aqueous hydrogen bromide is hydrogen bromide with a concentration of from about 25% to about 30%.

11. A process according to claim 1 wherein the compound of formula (I) is selected from the group consisting of
(3aS-cis)-1,2,3,3a,8,8a-hexahydro-1,3a,8-trimethylpyrrolo[2,3-b]indol-5-ol, (1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (1-methyl-1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (1-ethyl-1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (1-propyl-1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (1-butyl-1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (6-chloro-1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (7-chloro-1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (6-chloro-1-methyl-1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (7-chloro-1-methyl-1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (6-hydroxy-1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (7-hydroxy-1,2,3,4-tetrahydroisoquinolinyl)carbamate;
(3aS-cis)-1,2,3,3a,8,8a-hexahydro-1,3a,8-trimethylpyrrolo[2,3-b]indol-5-ol, (6-hydroxy-1-methyl-1,2,3,4-tetrahydroisoquinolinyl)carbamate; and
(3aS-cis)-1,2,3,3a,8,8a-hexahydro-1,3a,8-trimethylpyrrolo[2,3-b]indol-5-ol, (7-hydroxy-1-methyl-1,2,3,4-tetrahydroisoquinolinyl)carbamate.

12. A process according to claim 1 wherein said compound of formula (1) is (3aS-cis)-1,2,3,3a,8,8a-hexahydro-1,3a,8-trimethylpyrrolo[2,3-b]indol-5-ol, (1,2,3,4-tetrahydroisoquinolinyl)carbamate.

13. A process for the preparation of a product of formula (III)

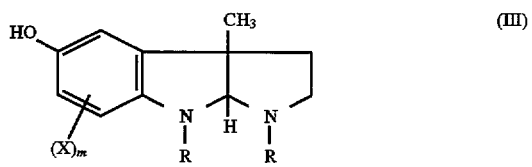

wherein

R is loweralkyl;

X is loweralkyl, loweralkoxy, halogen or trifluoromethyl; and m is 0, 1 or 2;

or a pharmaceutically acceptable salt thereof; comprising contacting a compound of formula (II)

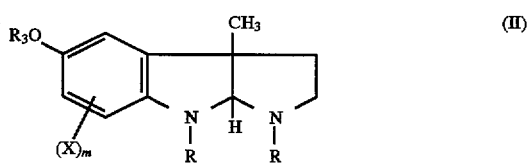

wherein

R, X and m are as defined above and $R_3$ is loweralkyl, with aqueous hydrogen bromide and lithium halide to afford a compound of formula (III).

14. A process according to claim 13 wherein said lithium halide is lithium bromide.

15. A process according to claim 13 wherein said lithium halide is lithium iodide.

16. A process according to claim 13 wherein R and $R_3$ are loweralkyl and X is hydrogen.

17. A process according to claim 16 wherein R is methyl and $R_3$ is methyl.

18. A process according to claim 17 wherein the compound of formula (II) is (−)-eserethole.

19. A process according to claim 13 wherein the compound of formula (III) is (−)-eseroline.

20. A process according to claim 13 wherein said aqueous hydrogen bromide is hydrogen bromide with a concentration within the range of from about 20% to about 50%.

21. A process according to claim 13 wherein said aqueous hydrogen bromide is hydrogen bromide with a concentration of about 48%.

* * * * *

UNITED STATES PATENT AND TRADEMARK OFFICE
CERTIFICATE OF CORRECTION

PATENT NO. : 5,677,457

DATED : October 14, 1997

INVENTOR(s) : Thomas B. K. Lee, Zhongli Gao, Barbara S. Rauckman

It is certified that error appears in the above-identified patent and that said Letters Patent is hereby corrected as shown below:

Column 4, Line 26 reads "hyroxymaleic" and should read --hydroxymaleic--.

Column 8, Line 58 reads " was add" and should read --was added--.

Column 11, Line 25 reads "NH4Br" and should read --$NH_4Br$--.

Column 11, Line 26 reads "Eta₃NHBr" and should read --$Et_3NHBr$--.

Signed and Sealed this

Fourteenth Day of December, 1999

Attest:

Q. TODD DICKINSON

Attesting Officer

Acting Commissioner of Patents and Trademarks